US012623029B2

(12) United States Patent
Carrel et al.

(10) Patent No.: US 12,623,029 B2
(45) Date of Patent: May 12, 2026

(54) SAFETY DEVICE FOR PREVENTING NEEDLE STICK INJURY WITH A NEEDLE OF A MEDICAL INJECTION DEVICE

(71) Applicant: Becton Dickinson France, Le Pont de Claix (FR)

(72) Inventors: Franck Carrel, Saint Jean de Vaulx (FR); Freddy Mills, Grenoble (FR)

(73) Assignee: Becton Dickinson France, Le Pont-de-Claix (FR)

( * ) Notice: Subject to any disclaimer, the term of this patent is extended or adjusted under 35 U.S.C. 154(b) by 934 days.

(21) Appl. No.: 17/620,159

(22) PCT Filed: Jun. 19, 2020

(86) PCT No.: PCT/EP2020/067181
§ 371 (c)(1),
(2) Date: Dec. 17, 2021

(87) PCT Pub. No.: WO2020/254624
PCT Pub. Date: Dec. 24, 2020

(65) Prior Publication Data
US 2022/0305214 A1     Sep. 29, 2022

(30) Foreign Application Priority Data

Jun. 21, 2019     (EP) .................................... 19305817

(51) Int. Cl.
*A61M 5/32*          (2006.01)
(52) U.S. Cl.
CPC ........ *A61M 5/3216* (2013.01); *A61M 5/3204* (2013.01)

(58) Field of Classification Search
CPC .................... A61M 5/3216; A61M 2005/3217
See application file for complete search history.

(56) References Cited

U.S. PATENT DOCUMENTS 5,662,617 A * 9/1997 Odell .................. A61M 5/3216
128/919
2002/0193744 A1* 12/2002 Alesi .................. A61M 5/3216
128/919
2018/0140780 A1 5/2018 Carrel

FOREIGN PATENT DOCUMENTS

CA      3046821 A1    5/2018
CN      102772840 B   6/2016
EP      0702973 B1   11/1999
(Continued)

*Primary Examiner* — Emily L Schmidt
(74) *Attorney, Agent, or Firm* — The Webb Law Firm

(57) ABSTRACT

A safety device for preventing needle stick injury comprises a ring configured to be attached to the distal tip of a medical injection device, a first hinge portion, and a protective shield. The protective shield comprises a second hinge portion pivotally coupled to the first hinge portion and is configured to adopt successively a storage position covering the needle tip, a retracted position uncovering the needle tip and a safety position covering the needle tip. In the safety position, the protective shield is locked on the ring by engagement of a locking member with a lug on the ring. The locking member is configured to engage the lug when the protective shield transitions from the retracted position to the safety position, passing from one side of the lug to the other, and remaining engaged with the lug for maintaining the protective shield in the safety position.

16 Claims, 15 Drawing Sheets

(56)      References Cited

FOREIGN PATENT DOCUMENTS

| | | | |
|---|---|---|---|
| EP | 1433419 | B1 | 5/2012 |
| WO | 2012071400 | A2 | 5/2012 |

* cited by examiner

SAFETY DEVICE FOR PREVENTING NEEDLE STICK INJURY WITH A NEEDLE OF A MEDICAL INJECTION DEVICE

CROSS-REFERENCE TO RELATED APPLICATIONS

This application is the United States national phase of International Application No. PCT/EP2020/067181 filed Jun. 19, 2020, and claims priority to European Patent Application No. 19305817.9 filed Jun. 21, 2019, the disclosures of which are hereby incorporated by reference in their entirety.

BACKGROUND

Technical Field

The present disclosure relates to a safety device for preventing needle stick injury with a needle of a medical injection device. The present disclosure also relates to a safety assembly comprising the safety device and a medical injection device.

Technical Background

Medical devices provided with sharp pointed needles are of daily practice among the medical community in order to perform injections or to take samples into or from muscles, veins or arteries. The medical devices may include injection devices such as syringes, pen-injectors, catheters or blood collection devices. Sharp pointed needles present an inherent risk of needle stick injury for the medical staff and the patients and are thus usually provided with a needle cap covering the needle before use. This cap not only preserves the needle from contamination, but also from undesired contacts or punctures that could occur during transport and delivery by the medical staff. Such a cap needs to be removed immediately before use of the medical device.

Replacing the needle cap onto the needle after use is strictly prohibited as it is regarded as a major cause of accidents and contamination for the medical staff. Indeed, the whole medical device or at least the used needle should be disposed of after use in an appropriate needle collector. However, a risk of needle stick injury still exists as the medical staff handles the bare, contaminated needles before disposal.

Safety devices have thus been designed to prevent needle stick injury with the needle of such medical devices after use, i.e. between the end of the injection or collection and the proper disposal of the device. Usually, such safety systems are designed to be locked automatically or manually on at least the needle tip when the medical act is finished. Examples of such safety devices are given in EP0702973 and CA3046821.

Nevertheless, many of these safety systems require a triggering step in order to expose the needle tip before use, which slows down the pace of the medical act and decreases the safety level of the medical device. In addition, the majority of such safety systems increase the overall size of the device leading to difficult handling but also to storage concerns, particularly for prefilled syringes. Finally, most of these systems do not achieve a complete exposure of the needle tip and impede the medical act by preventing direct view and access to the needle tip.

Additionally, pre-fillable syringes are transported in sterile packaging after manufacturing in order to be filled by the pharmaceutical companies with a pharmaceutical product before the final delivery to the medical staff. The sterile packaging is adapted to the length and diameter of the syringe closed with a usual needle cap and may not accept oversized safety devices as currently available.

SUMMARY

According to non-limiting embodiments or aspects of the present disclosure, provided is a safety device which prevents the user, the patient, or any person around the device, from coming into contact with the needle of the medical injection before and after use of the device, that is, before and after the injection has been performed. In that way, the needle, especially the needle tip, is not physically accessible, and the risk of accidental pricks or wounds generally caused by contact of the needle with a person close to the device is nullified.

The present disclosure aims also to provide a safety device that is readily usable, which presents a simplified structure compared to the known devices, and a size suitable for the transport in sterile packaging. To this end, according to non-limiting embodiments or aspects of the present disclosure, provided is a safety device for preventing needle stick injury with a needle extending from a distal tip of a medical injection device. The safety device may include a ring configured to be attached to the distal tip of the medical injection device. The ring may include a first hinge portion. The safety device may include a protective shield comprising a second hinge portion pivotally coupled to the first hinge portion. The protective shield is configured to adopt successively a storage position wherein the protective shield covers the needle tip, a retracted position wherein the protective shield uncovers the needle tip and a safety position wherein the protective shield covers the needle tip. The ring may include a lug, the lug extending distally and comprising a radially inward side and a radially outward side opposite to the radially inward side relative to the axis of the ring.

The protective shield may include at least one proximal locking member. In the safety position, the protective shield is locked on the ring by engagement of the locking member with the lug. The locking member is configured to engage the lug when the protective shield transitions from the retracted position to the safety position, so that the locking member passes from the radially outward side of the lug to the radially inward side of the lug, and remains engaged with the lug for maintaining the protective shield in the safety position.

According to non-limiting embodiments or aspects, provided is a safety device for preventing needle stick injury with a needle extending from a distal tip of a medical injection device, comprising a ring configured to be attached to the distal tip of the medical injection device and a protective shield. The ring may include a first hinge portion. The protective shield may include a second hinge portion pivotally coupled to the first hinge portion. The protective shield is configured to adopt successively a storage position wherein the protective shield may cover the needle tip, a retracted position wherein the protective shield uncovers the needle tip, and a safety position wherein the protective shield covers the needle tip. The ring may include a lug, the lug extending distally. The lug may include a radially inward side and a radially outward side opposite to the radially inward side relative to the axis of the ring.

The protective shield may include at least one proximal locking member. In the safety position, the protective shield may be locked on the ring by engagement of the locking member with the lug. The first and second hinge portions are configured so that at least a part of the first and/or second hinge portions may be subject to flexural deformation by engagement of the locking member with the lug during transition from the retracted position to the safety position and may be subject to buckling deformation in the safety position to impede disengagement of the locking member from the lug.

The safety device may allow the user to carry out the injection of a pharmaceutical composition to a patient or the user, while preventing any person in the vicinity of the device, in particular the patient and the user, to contact the needle of the medical injection device, thereby avoiding injuries and making the injection device safe. In both storage position and safety position, the protective shield may cover at least the tip of the needle, thereby preventing any contact between the needle tip and any person around the medical injection device. In the safety position, the protective shield may be locked on the ring, which may prevent the protective shield from moving back to the storage position or the retracted position, thereby further securing the device. In the retracted position, the protective shield may uncover the needle tip, thereby allowing the needle to be positioned into the skin of the patient and the injection to be carried out.

According to non-limiting embodiments or aspects, provided is a safety device wherein the locking member may include a single flexible tab configured to deflect radially outwardly from a body of the protective shield when the protective shield transitions from the retracted position to the safety position. The locking member may include two flexible tabs separated by a slot, configured to deflect radially outwardly from a body of the protective shield when the protective shield transitions from the retracted position to the safety position.

Each flexible tab may include a free end separated from the body of the protective shield by a respective groove opposite the slot. The flexible tab may extend axially and proximally from the body of the protective shield. The flexible tab may protrude proximally from the lug when the protective shield is in the storage position and/or in the safety position. The flexible tab may extend toward the second hinge portion. The flexible tab may include an inner surface provided with a rib, and the ring may include a protrusion provided with a cam member. The protrusion may extend radially from the ring and may include a distal side and a proximal side located proximally relative to the distal side. The flexible tab is configured to deform in flexion by engagement of the rib with the cam member when the protective shield transitions from the storage position to the retracted position, so that the rib may pass from the distal side of the lug to the proximal side of the lug. The rib is configured to remain engaged with the cam member for maintaining the protective shield in the retracted position.

The flexible tab may include an inner surface provided with a rib, and the ring may include a protrusion provided with a cam member, the protrusion extending radially from the ring. The protrusion may include a distal side and a proximal side located proximally relative to the distal side. The flexible tab and the protrusion being configured so that the flexible tab is subject to flexural deformation by engagement of the rib with the cam member during transition from the storage position to the retracted position, and subject to friction with the cam member by frictional engagement of the rib with the cam member in the retracted position to maintain the protective shield in the retracted position.

The rib and the cam member are configured to maintain the protective shield at an angle superior or equal to 80° relative to an axis of the ring when the protective shield is in the retracted position. The first hinge portion may include a groove defining a pivot axis of the protective shield, and the protective shield may include an axle clipped into the groove. The first hinge portion may include two colinear pins defining a pivot axis of the protective shield, and the protective shield may include two proximal legs provided with an opening, each pin engaging a respective opening.

The protective shield may include at least a hook which may be configured to engage the needle so as to lock the needle relative to the protective shield when the protective shield is in the safety position.

The safety device may include a protective cap which may be configured to be mounted onto the distal tip of the medical injection device to cover at least the needle tip, wherein the protective shield may be interlocked with the protective cap when the protective shield is in the storage position.

According to non-limiting embodiments or aspects, provided is a safety assembly comprising a medical injection device comprising a barrel, a distal tip extending distally from the barrel, and a needle mounted into the distal tip, and a safety device as described previously, wherein the ring is around the distal tip of the medical injection device.

According to non-limiting embodiments or aspects, the rib and the cam member are configured so that, when the protective shield is in the retracted position, the distal end of the protective shield does not protrude from the needle tip.

In the present disclosure, the "distal direction" is to be understood as meaning the direction of injection, with respect to the medical container onto which the safety device of the invention is to be mounted onto. The distal direction corresponds to the travel direction of a plunger positioned at least partially inside the barrel of the injection device during the injection, the pharmaceutical composition contained initially in the barrel being expelled from the barrel. Terms related to the distal direction, such as "distal", or "distally" also relate to the direction of injection. The "proximal direction" is to be understood as meaning the opposite direction to the direction of injection. Terms related to the proximal direction, such as "proximal", or "proximally" also relate to the opposite direction to the direction of injection. A first element of the safety device or the safety assembly that is located further on the plunger path than a second element is thus distal or located distally relative to the second element. On the contrary, a first element of the safety device or the safety assembly that is located closer on the plunger path than a second element is thus proximal or located proximally relative to the second element.

In the present disclosure, the "injection process" correspond to the use of the medical injection device for performing the injection of a composition contained therein, from the handling by the user of the stored injection device previously filled with the composition to be injected, to the disposal of the empty medical injection device after the injection has been performed. Such injection process comprises especially the steps of handling the stored medical injection device, positioning the medical injection device in the vicinity of the skin of the patient, pricking the skin of the patient, injecting the composition, removing the needle from the skin of the patient, and disposing of the needle.

BRIEF DESCRIPTION OF THE DRAWINGS

Further features and advantages will become apparent from the detailed description to follow, with reference to the appended drawings, in which.

DETAILED DESCRIPTION

The present disclosure relates to a safety device for preventing a user, especially a healthcare professional, from pricking himself or any person around, such as a patient to be treated, with the needle of a medical injection device, such as a syringe or the like, after injection.

Figure 3A:
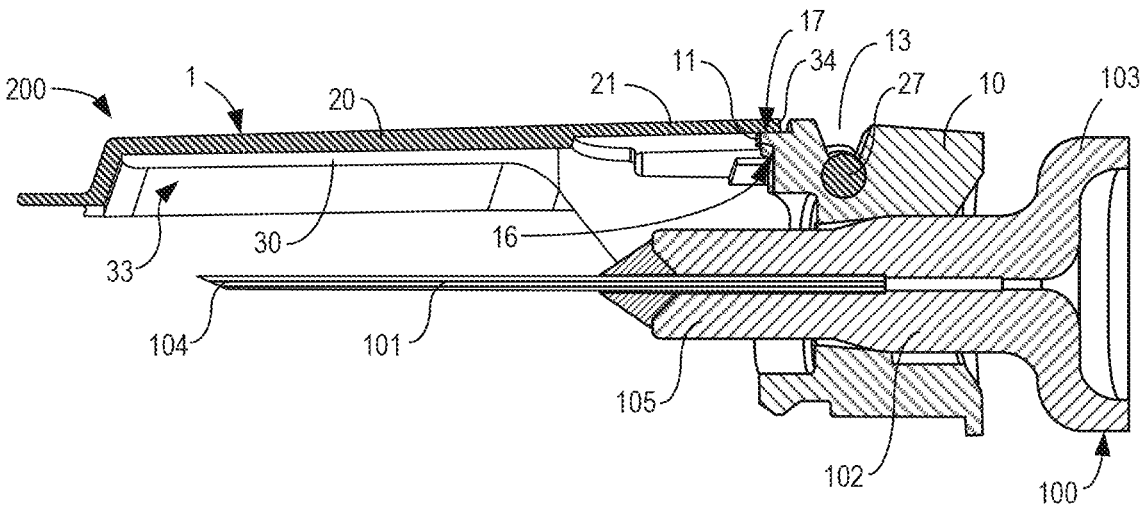
FIG. 3A is a side sectional view of a safety device centered onto the distal tip of the medical injection device, wherein the ring is attached to the distal tip and the protective shield, which is pivotably mounted onto the ring, is in the storage position.

Referring to FIG. 3A, the safety device 1 may include a ring 10 which is configured to be attached to the distal tip 102 of the barrel 103 of the medical injection device 100. The barrel 103 may be a container for a medical composition to be injected into the patient. The safety device 1 may include a protective shield 20 pivotably coupled to the ring 10. The composition is a fluid, and may be a liquid such as a pharmaceutical drug, a vaccine, etc. When attached together, the safety device 1 and the medical injection device 100 form a safety assembly 200.

The protective shield 20 is configured to act as a physical barrier which, depending on the step of the injection process, may prevent the user and any person around from contacting the needle 101, especially the needle tip 104, thereby preventing potential pricking injuries.

A non-limiting embodiment of the safety device 1 is illustrated in FIG. 3A. As shown in FIG. 3A, the safety device 1 may include the ring 10 illustrated in FIG. 1 and the protective shield 20 illustrated in FIG. 2.

Figure 1:
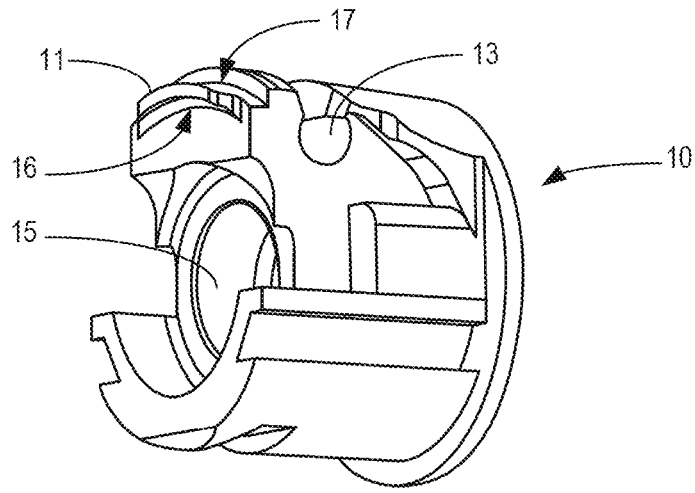
FIG. 1 is a general perspective view of the ring according to a non-limiting embodiment of the safety device.

In reference to FIG. 1, the ring 10 may have a substantially cylindrical shape, and may extend about an axis. In the present disclosure, the term "axially" refers to the ring 10 axis or to an axis parallel to the ring 10 axis. The ring 10 is configured to be attached onto a distal tip 102 of barrel 103. Alternatively, the ring 10 may be integrated into the distal tip 102 of a plastic barrel.

As shown in FIG. 1, the body of the ring 10 is pierced by a through hole 15 that may extend substantially centrally relative to the body. The through hole 15 is adapted to accommodate the distal tip 102 of the medical injection device, as visible in FIG. 3A. When inserted into the through hole 15 of the ring 10, an end portion 105 of the distal tip 102 protrudes from the ring 10, and the needle 101 protrudes from the end portion of the distal tip 102.

Referring now to FIG. 3A, the ring 10 may include a first hinge portion and a lug 11 which protrudes from the outer surface of the ring 10 body. In some non-limiting embodiments or aspects, the lug 11 extends axially. As shown in FIG. 3A, the lug 11 may protrude distally from the ring 10 body.

According to non-limiting embodiments or aspects, the first hinge portion may include a groove 13 formed in the outer surface of the ring 10. The groove 13 defines a pivot axis about which the protective shield 20 is pivotable.

As particularly visible in FIG. 3A, the lug 11 may be located distally relative to the groove. Moreover, the lug 11 may extend perpendicularly to the axis of the groove.

The ring 10 may be made of any rigid polymer adapted to medical use, such as high-density polyethylene (PE), polypropylene (PP), polycarbonate (PC), acrylonitrile butadiene styrene (ABS), polyoxymethylene (POM), polystyrene (PS), polybutylene terephthalate (PBT), polyamide (PA), and their combinations.

The protective shield 20 may be made of any rigid polymer adapted to medical use, such as high-density polyethylene (PE), polypropylene (PP), polycarbonate (PC), acrylonitrile butadiene styrene (ABS), polyoxymethylene (POM), polystyrene (PS), polybutylene terephthalate (PBT), polyamide (PA), and their combinations.

Figure 2:
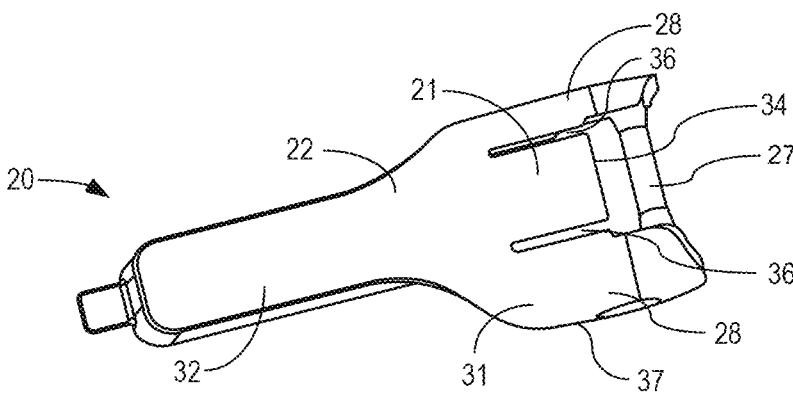
FIG. 2 is a general perspective view of the protective shield according to a non-limiting embodiment.

In reference to FIG. 2, the protective shield 20 may include proximal portion 31 and a distal arm 32 that may extend distally from the proximal portion. The proximal portion 31 may include two proximal legs 28 which may face each other, and which may rejoin at the distal projection. Each of the proximal legs may be provided with a cam surface 37.

The distal projection 32 may include a notch 33 configured to accommodate at least the tip 104 of the needle of the medical injection device in a safety position, when the safety device 1 is mounted onto the distal tip 102 of the medical injection device 100, as shown in FIG. 3A. The safety position will be defined in the following of the text. The notch 33 extends along the distal projection 32, parallel to the needle accommodated therein. The distal projection 32 may include an inner surface 30. The distal projection 32 may be provided with one or several hook(s) configured to engage the needle 101, so as to lock the protective shield 20 relative to the needle. The hook(s) may be provided on the inner surface 30 of the distal projection 32. When the distal projection 32 is provided with a notch 33, the hook(s) may extend from the inner surface of the notch 33.

Referring now to FIG. 2, the protective shield 20 may include a second hinge portion that is configured to be pivotally coupled to the first hinge portion of the ring 10. According to non-limiting embodiments or aspects, the second hinge portion may include an axle 27 which may extend between the two proximal legs 28 of the proximal portion 31, thereby joining the proximal legs 28. The axle 27 may be adapted to be clipped into the groove 13 of the ring 10 while being pivotable relative to the ring 10. The axle 27 and the groove 13 thereby may form a hinge wherein the protective shield 20 is pivotally movable relative to the ring 10 around the pivot axis.

Referring now to FIG. 3A, the protective shield 20 may include a locking member that is configured to engage the lug 11 of the ring 10. According to non-limiting embodiments or aspects, the locking member comprises a single flexible tab 21 that may be adapted to deform to pass from a radially outward side 17 of the lug 11 to a radially inward side 16 of the lug 11 opposite the radially outward side 17 relative to the lug 11, in a substantially radial direction. In some non-limiting embodiments or aspects, the flexible tab 21 may extend in the proximal direction, and may be separated from the two proximal legs 28 by two respective slots 36 that delimit the flexible tab 21. The flexible tab 21 may extend from the join of the two proximal legs 28, between the proximal legs 28, toward the axle 27. The flexible tab 21 may extend proximally from the distal projection 32 toward the axle 27.

The safety device 1 may include a protective cap 50 configured to be mounted onto the distal tip 102 of the medical injection device 100 to cover at least the needle tip 104. The safety device 1 may include a sealing cap (not represented), made in elastomeric material, and configured to accommodate the distal tip 102 of the medical injection device 100 and the needle tip 104. The sealing cap is enclosed in the protective cap. Non-limiting embodiments of the protective cap and the sealing cap are described in the document US 2018/0140780. A non-limiting embodiment of the protective cap 50 is illustrated in FIG. 7.

Figure 7:
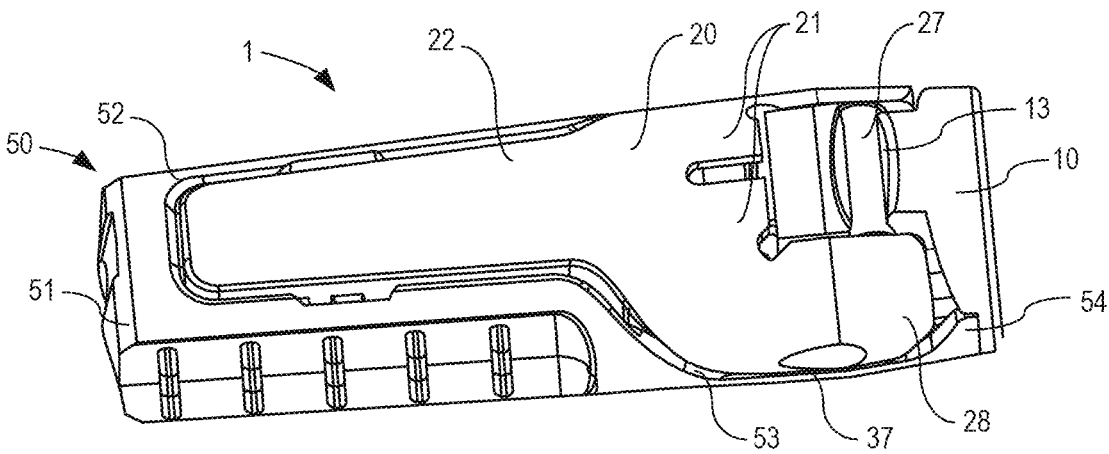
FIG. 7 is a general view of the safety device of a non-limiting embodiment, provided with a protective cap.

Referring now to FIG. 7, the protective cap 50 may include a tubular body 51 that defines an inner cavity, a distal radial opening 52 and a top proximal extension contiguous to the distal radial opening 52. The protective cap may include a bottom proximal extension, parallel to the top proximal extension when present, provided with two curved cuts 53 and two engaging pegs 54. The protective cap 50 may be made in the same material as the ring 10. It may be either opaque or transparent.

The protective cap 50 is designed to be complementary and interlocked with the protective shield 20 and the ring 10 when the protective shield 20 is in the storage position. The protective shield 20 and the protective cap 50 may be dimensioned and interlocked such that the two curved cuts 53 of the protective cap 50 may accommodate the cam surfaces 37 of the proximal legs 28 while the two engaging pegs 54 of the protective cap 50 engage the cam surfaces 37.

The protective cap 50, the protective shield 20, and optionally the ring 10 and/or the sealing cap, may be totally interlocked in an example of a safety device 1. The safety device 1 may be provided as a pre-assembled sub-unit for a straightforward mounting on the distal tip 102 of the medical injection device 100. The mounting step may be done as a single step by application of a fitting force directed axially toward the distal tip 102 of the medical injection device 100 for arrangement of the safety device 1 onto the distal tip 102.

The safety device 1 is configured so that removal of the protective cap 50 may cause the protective shield 20 to pivot about its axis of rotation, corresponding to the axis of the hinge, in a direction opposite to the needle 101, i.e. towards the proximal direction.

The protective shield 20 is configured to adopt different positions with respect to the ring 10, and with respect to the distal tip 102 and the needle 101 of the medical injection device 100, by pivoting about the pivot axis, depending on the step of the injection process. The protective shield 20 is configured to adopt successively a storage position wherein the protective shield 20 covers the needle tip 104 without being locked on the lug 11, a retracted position wherein the protective shield 20 uncovers the needle tip 104, and a safety position wherein the protective shield 20 covers the needle tip 104 and is locked on the lug 11. These positions of the protective shield 20 and the transitions between them will now be described along with the functioning of the safety device 1, in the following of the present disclosure, in reference to FIGS. 3A, 3B, and 3C.

FIG. 3A corresponds to the configuration of the safety device 1 before its use. In this configuration, the protective shield 20 is in the storage position wherein it covers the needle tip 104. In the storage position, the protective shield 20 is interlocked with the protective cap 50 when present, and substantially parallel to the needle 101, which is enclosed in the protective cap 50. Furthermore, the needle tip 104 is embedded in the elastomeric material of the elastomeric inner cap, thereby avoiding any leakage of the contents of the container of the medical injection device 100. The protective cap 50 may protect the needle 101 prior to use, for example from shocks, dust, and contact with any person around or any contaminations. The elastomeric inner cap maintains the sterility and the sealing of the needle 101.

As illustrated in FIG. 3A, the needle 101 is parallel to the axis of the ring 10. The longitudinal axis of the protective shield 20 may be parallel to the axis of the ring 10. The flexible tab 21 may be parallel to the axis of the ring 10. The flexible tab 21 may be located radially outwardly from the lug 11, relative to the axis of the ring 10, and may cover the radially outward side 17 of the lug 11.

In order to use the safety assembly 200, the user draws the protective cap 50 in the distal direction. The removal of the protective cap 50 triggers the rotation of the protective shield 20 around the hinge, away from the storage position.

Figure 3B:
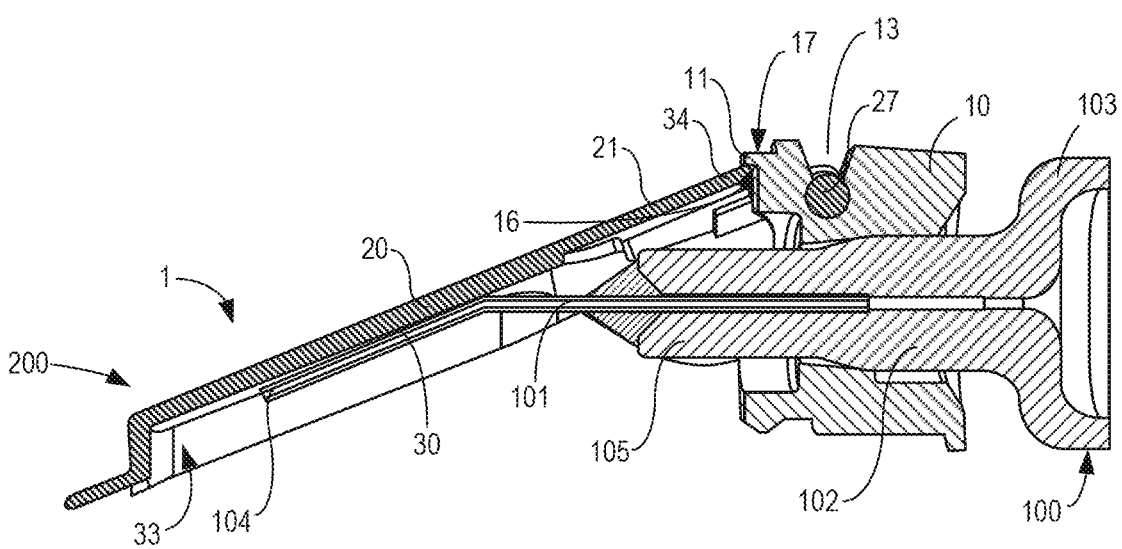
FIG. 3B is a side sectional view of a safety device of FIG. 3A, wherein the protective shield is in the safety position.
Figure 3C:
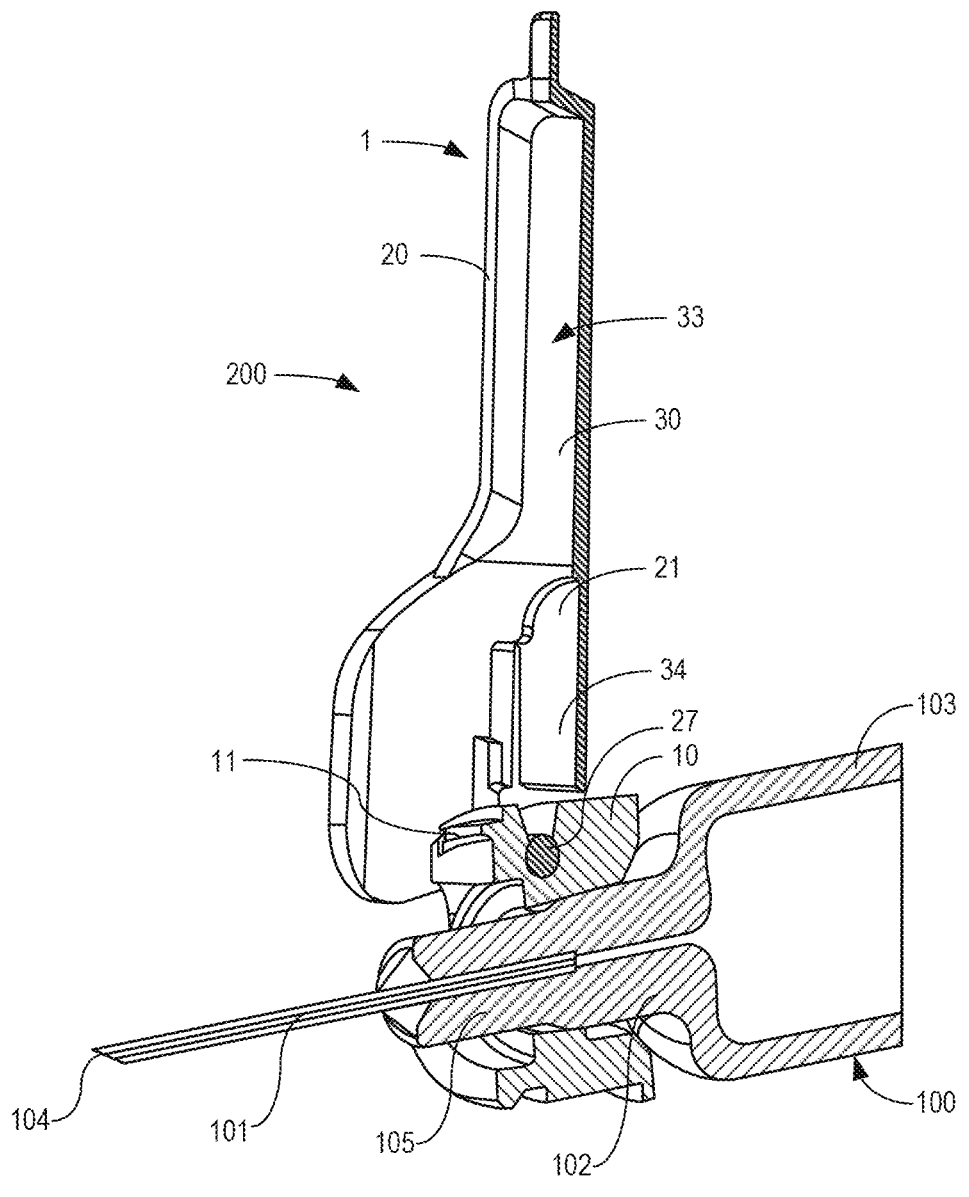
FIG. 3C is a side sectional view of a safety device of FIG. 3A, wherein the protective shield is in the retracted position.

The protective shield 20 may further rotate up to the retracted position illustrated in FIG. 3C. The safety device 1 is configured so that removal of the protective cap 50 may cause the protective shield 20 to pivot about the hinge up to its retracted position. In more details, as soon as the protective cap 50 moves distally, the engaging pegs 54 of the protective cap 50 may push onto the cam surfaces 37 of the protective shield 20, which results in the rotary opening movement of the protective shield 20 towards the barrel 103 of the medical injection device 100. The rotary movement of the cam surfaces 37 may be optimized by the specific shapes of the curved cuts 53 which may allow a smooth and natural movement, similar to the opening of a needle cap that does not have any safety devices.

In the retracted position, the needle tip 104 may be uncovered and physically accessible, and the safety assembly 200 may be ready for the injection of the composition contained in the medical injection device 100. The protective shield 20 extends obliquely, or perpendicularly, relative to the axis of the ring 10. The angle between the protective shield 20 and the ring 10 may be adjusted by the user, and may be inferior, equal, or superior to 80°, preferably to 90°. To that end, the movement of the pivot axle 27 in the groove 13 of the ring 10 may be frictional, and the friction may be sufficient to maintain the protective shield 20 in the position the user moved the protective shield into, with no further actuation of the protective shield 20 by the user. Such position may be the retracted position, or any position between the storage position and the retracted position.

As illustrated in FIG. 3C, the longitudinal axis of the protective shield 20 may be oblique or substantially perpendicular to the axis of the ring 10. The flexible tab 21 may be oblique or perpendicular to the axis of the ring 10. The flexible tab 21 may remain located radially outwardly relative to the lug 11, with regard to the axis of the ring 10, and the proximal end 34 of the flexible tab 21 may face the groove 13 of the ring 10 and the axle 27 accommodated therein.

Once the injection has been performed, the user may pivot the protective shield 20 around the pivot axis, towards the needle 101, into the safety position illustrated in FIG. 3B. The needle tip 104 may be covered by the protective shield 20, and any pricking of the user or any person around by the needle tip may be prevented. Rotation of the protective shield 20 around the pivot axis may cause the flexible tab 21 to engage the lug 11 of the ring 10. The flexible tab 21 is located radially outwardly from the lug 11, relative to the axis of the ring 10, and abuts the radially outward side 17 of the lug 11. The flexible tab 21 may be subjected to flexural deformation by deflecting radially outwardly from the body 22 of the protective shield 20. In other terms, the flexible tab lifts slightly.

Further rotation of the protective shield 20 causes the flexible tab 21 to slide on the lug 11 of the ring 10, until the flexible tab 21 passes the lug 11, and gets to the other side of the lug 11, called radially inward side 16 of the lug 11. At the end of the rotating movement, the protective shield 20 is in the safety position, and covers at least the needle tip 104.

As illustrated in FIG. 3B, the longitudinal axis of the protective shield 20 may be oblique relative to the axis of the ring 10. The flexible tab 21 may be oblique relative to the axis of the ring 10. The flexible tab 21 may be located radially inwardly relative to the lug 11, with regard to the axis of the ring 10, and the proximal end 34 of the flexible tab 21 may face the lug 11. The needle 101 may be locked into the protective shield 20 by the hook, and the needle tip 104 may be accommodated inside the notch 33, as visible in FIG. 3B. Therefore, the needle tip 104 is covered and any pricking of a person by the needle is prevented.

The protective shield 20 may be prevented from moving from the safety position, in particular from moving back to the storage position or the retracted position, by abutment of the proximal end 34 of the flexible tab 21 against the lug 11 which may cause the flexible tab 21 to undergo buckling deformation. This buckling deformation may impede disengagement of the flexible tab 21 from the lug 11. As a consequence, the protective shield 20 may be secured in the safety position, and the safety device 1 may no longer be used for another injection. Hence, the user may put the safety assembly 200 in a bin adapted for this purpose, or may remove the safety device 1 from the medical injection device 100 before putting them into adapted bins, without physically exposing him or any person around to the needle tip. Any risk of needle stick injury is thus prevented.

When abutting the needle 101, the protective shield 20 may be further pushed by the user to continue the rotating movement, so that at least the needle tip 104 deforms under the pressure exerted by the user. This position also corresponds to the safety position. As a consequence, the deformed needle tip 104 lies inside the notch 33, parallel to and in contact with the inner surface 30 of the notch 33, which may further improve the safety by totally covering the needle tip 104.

Figure 4:
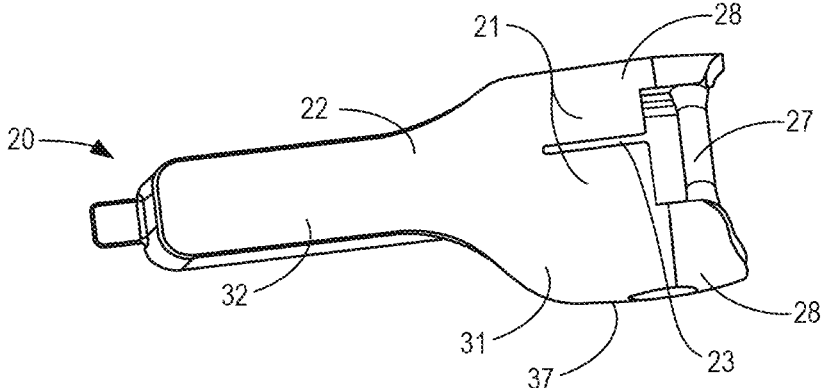
FIG. 4 is a general perspective view of the protective shield according to a non-limiting embodiment of the safety device.
Figure 5A:
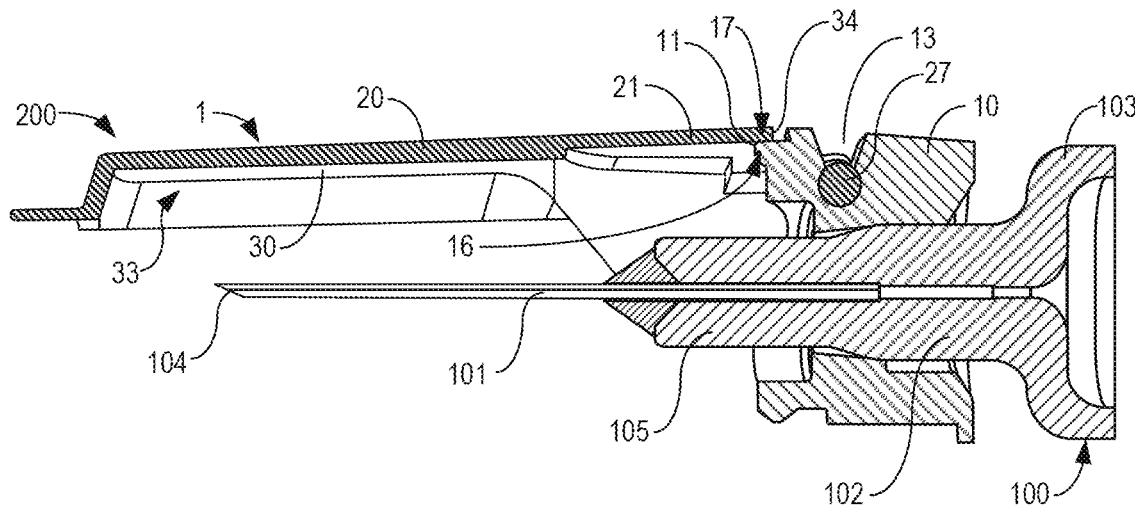
FIG. 5A is a side sectional view of a safety device centered onto the distal tip of the medical injection device, wherein the ring is attached to the distal tip and the protective shield, which is pivotably mounted onto the ring, is in the storage position.
Figure 5B:
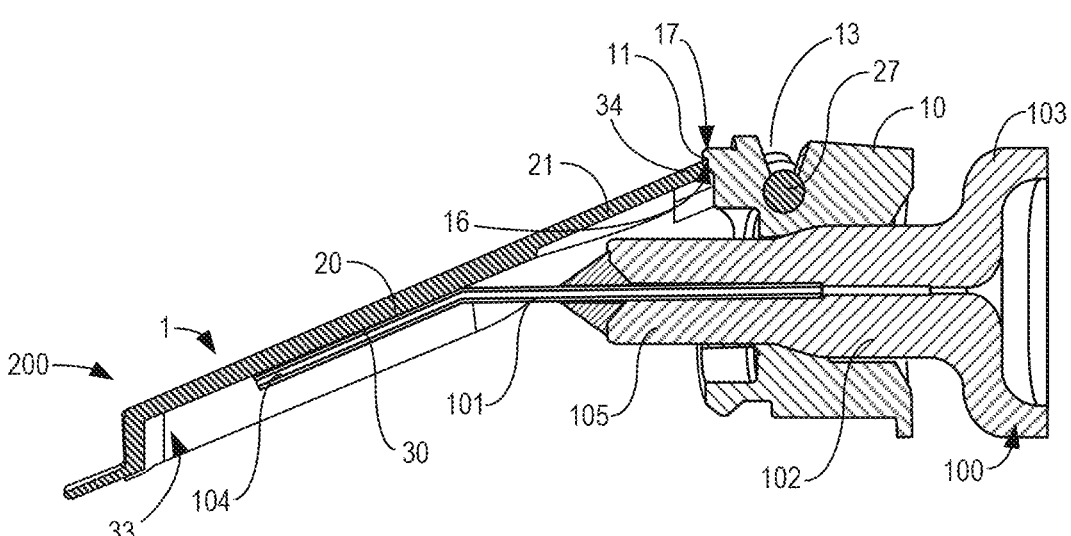
FIG. 5B is a side sectional view of a safety device of FIG. 5A, wherein the protective shield is in the safety position.
Figure 5C:
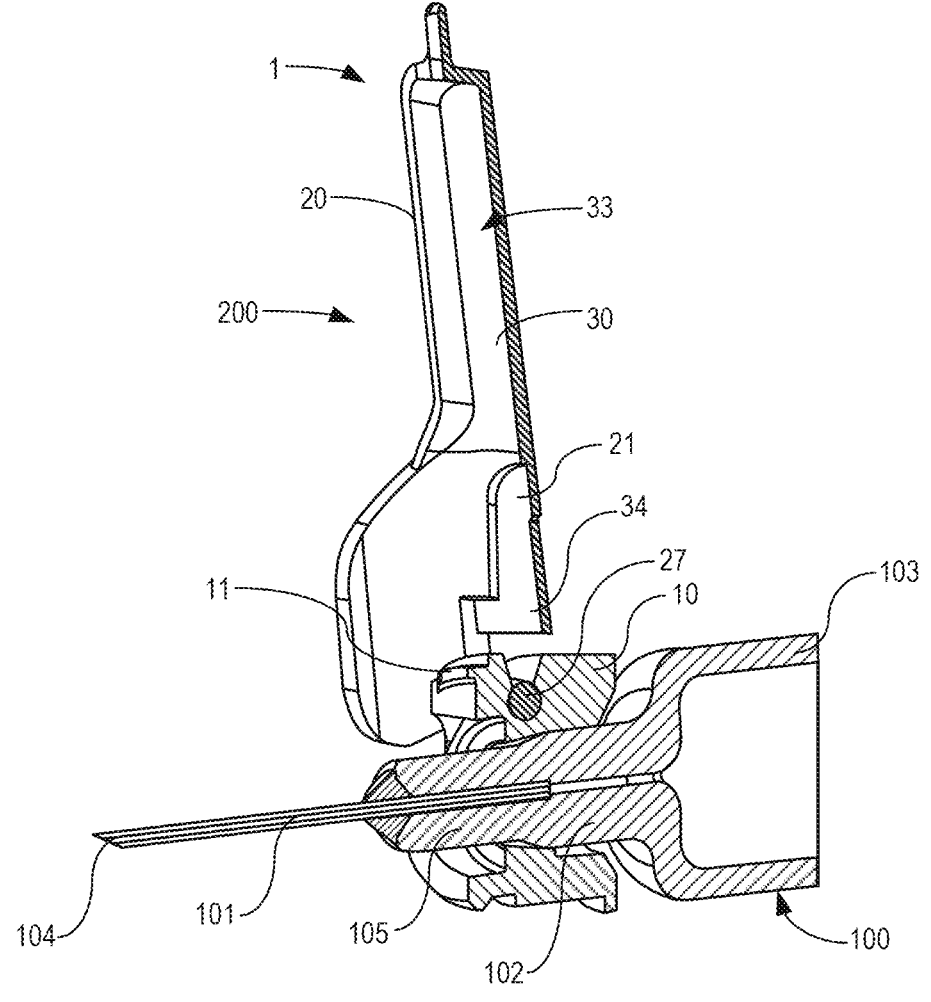
FIG. 5C is a side sectional view of a safety device of FIG. 5A, wherein the protective shield is in the retracted position.

A non-limiting embodiment of the safety device 1 is illustrated in FIGS. 5A, 5B, and 5C, wherein the safety device 1 may include the ring 10 illustrated in FIG. 1 and the protective shield 20 illustrated in FIG. 4. The ring 10 shown in FIGS. 5A, 5B, and 5C may be the same as or similar to the ring 10 in non-limiting embodiments previously described. The general structure of the protective shield 20 of this non-limiting embodiment may be the same as or similar to that of non-limiting embodiments described before, and will not be further described. The common features between the non-limiting embodiments represented in FIGS. 1, 2, 3A-C and 4, 5A-C are given the same references.

Figure 6:
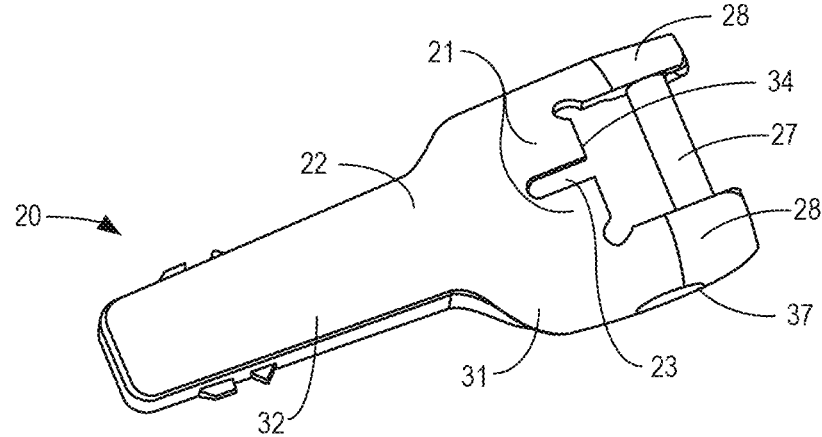
FIG. 6 is a general perspective view of the protective shield according to another non-limiting embodiment.

The locking member may include two flexible tabs 21 separated by a slot 23. Non-limiting embodiments of the protective shield 20 provided with two flexible tabs 21 is illustrated in FIG. 6, wherein each flexible tab 21 may include a free end 34 separated from the body 22 of the protective shield 20 by a respective groove 24 opposite the slot 23. The dimensions of the grooves 24 may be adapted to adjust the flexibility and the deformation of each of the flexible tabs 21.

The functioning of the safety device 1 according to a non-limiting embodiment may be similar to that of other non-limiting embodiments, except that the transition of the protective shield 20 from the retracted position to the safety position causes both flexible tabs 21 to engage the lug 11 of the ring 10. As a result, the two flexible tabs 21 may deflect radially outwardly from the body 22 of the protective shield 20 and may slightly deviate from each other relative to the slot 23 in-between. This may make the transition between the retracted position and the safety position smoother compared to other non-limiting embodiments.

Figure 8:
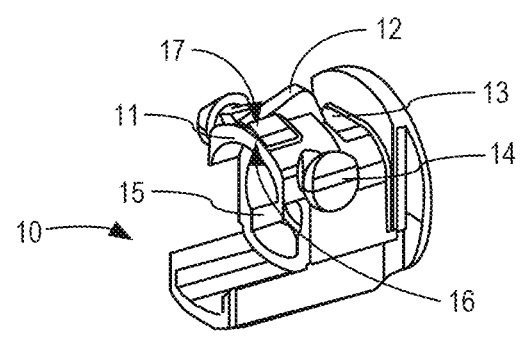
FIG. 8 is a general perspective view of the ring according to a non-limiting embodiment.
Figure 9:
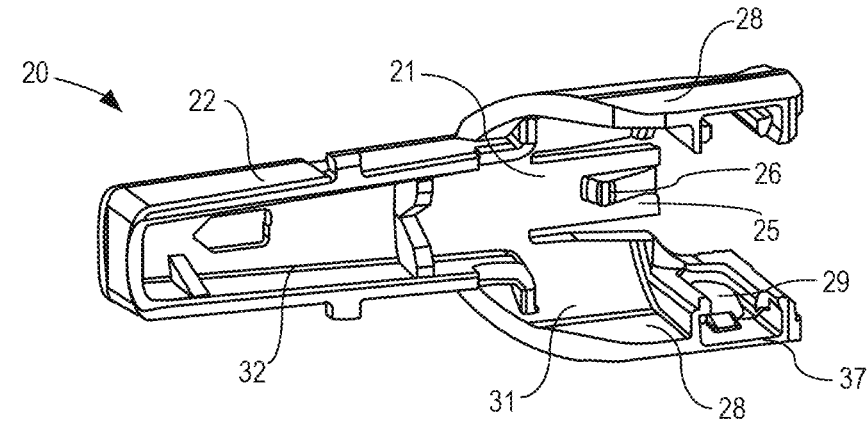
FIG. 9 is a general perspective view of the protective shield according to a non-limiting embodiment.

A non-limiting embodiment of the safety device 1 is illustrated in FIGS. 9, 10A-C, and 11A-C, wherein the safety device 1 may include the ring 10 illustrated in FIG. 8 and the protective shield 20 illustrated in FIG. 9. The general structures of the ring 10 and protective shield 20 of this non-limiting embodiment may be the same as or similar to that of non-limiting embodiments described before, and will not be further described. The common features between non-limiting embodiments represented in FIGS. 1, 2, 3A-C and 8-10, 11A-C, and 12A-C are given the same references.

Figure 10:
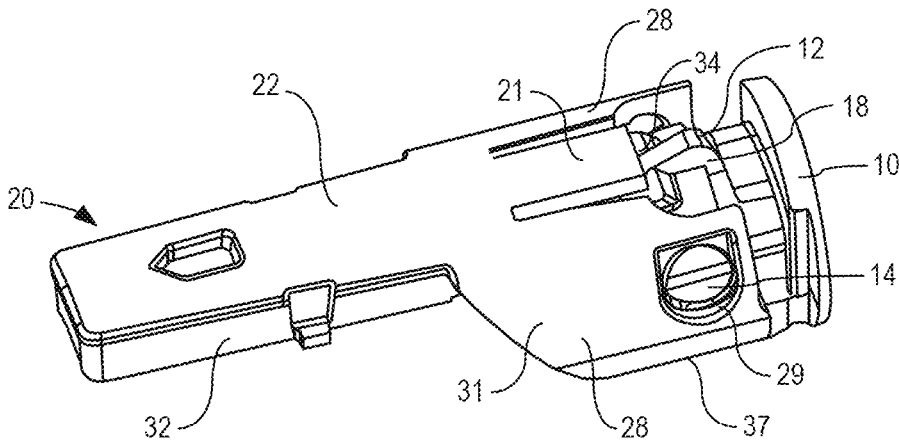
FIG. 10 is a general view of the safety device comprising the protective shield of FIG. 9 pivotably mounted onto the ring of FIG. 8.

According to non-limiting embodiments shown in FIG. 8-10, the first hinge portion of the ring 10 may include two colinear pins 14 that define a pivot axis of the protective shield 20.

The ring 10 may include a lug 11 which protrudes from the outer surface of the ring 10, a protrusion 18 provided with a cam member 12, and a groove 13. The second hinge portion of the protective shield 20 may include two openings 29, each opening 29 being provided in one of the two proximal legs 28 of the proximal part of the protective shield 20. Each pin 14 is configured to engage a respective opening 29, thereby forming a hinge wherein the protective shield 20 is pivotably movable relative to the ring 10 around a pivot axis joining the centers of the pins 14.

The locking member of the protective shield 20 may include a single flexible tab 21 that may be adapted to deform when engaging the lug 11 of the ring 10. The flexible tab 21 may include an inner surface 25 provided with a rib 26. The rib 26 may be adapted to engage the cam member 12 when the protective shield 20 transitions from the storage position to the retracted position.

Figure 11A:
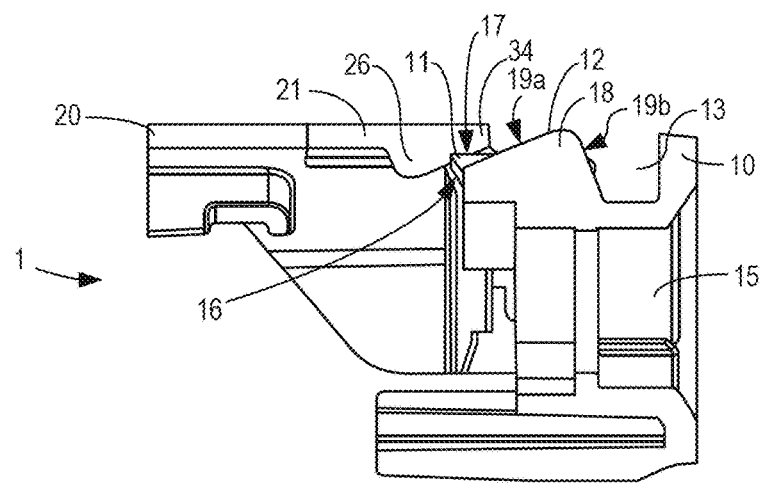
FIG. 11A is a side sectional view of the safety device, wherein the protective shield is in the storage position.

The functioning of the safety device 1 according to the non-limiting embodiments will now be described, in reference to FIGS. 11A-C and 12A-C. FIG. 11A corresponds to the configuration of the safety device 1 before its use. In this configuration, the protective shield 20 may be in the storage position wherein it covers the needle tip 104. The needle 101 may be parallel to the axis of the ring 10. The longitudinal axis of the protective shield 20 may be parallel to the axis of the ring 10. The flexible tab 21 may be parallel to the axis of the ring 10. The flexible tab 21 may be located radially outwardly from the lug 11, relative to the axis of the ring 10, and may contact the radially outward side of the lug 11.

Figure 11B:
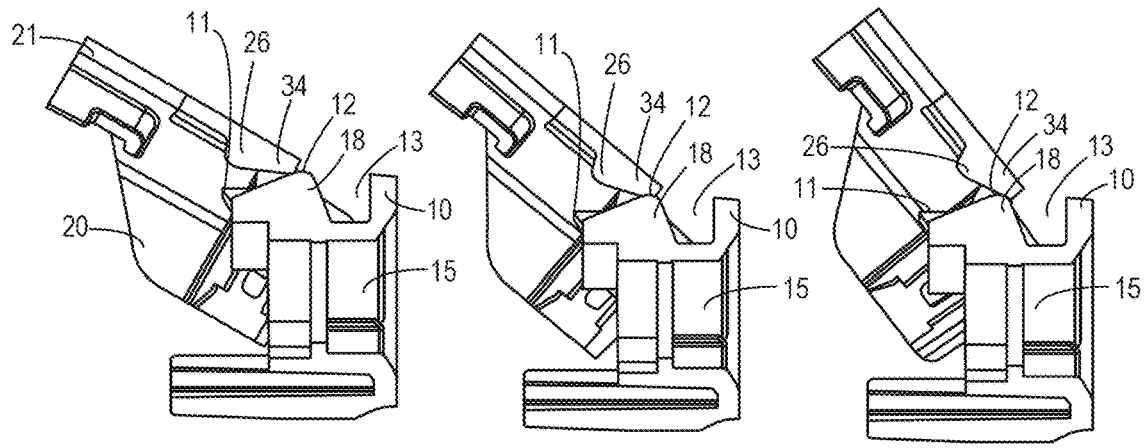
FIG. 11B illustrates the transition of the protective shield from the storage position to the retracted position.

In order to use the safety assembly 200, the user draws the protective cap 50 in the distal direction. The removal of the protective cap 50 may trigger the rotation of the protective shield 20 around the pivot axis of the hinge, relative to the pins 14 of the ring 10, away from the storage position (FIG. 11B). The protective shield 20 may further rotate up to the retracted position illustrated in FIG. 11C. The safety device 1 is configured so that removal of the protective cap 50 causes the protective shield 20 to pivot about the hinge up to its retracted position. Rotation of the protective shield 20 around the pivot axis may cause the rib 26 of the flexible tab 21 to engage the cam member 12 of the ring 10. The flexible tab 21 may abut a distal side 19*a* of the protrusion 18. The flexible tab 21 may be subjected to flexural deformation by deflecting radially outwardly from the body 22 of the protective shield 20, which may be caused by the engagement of the rib 26 with the cam member 12.

Figure 11C:
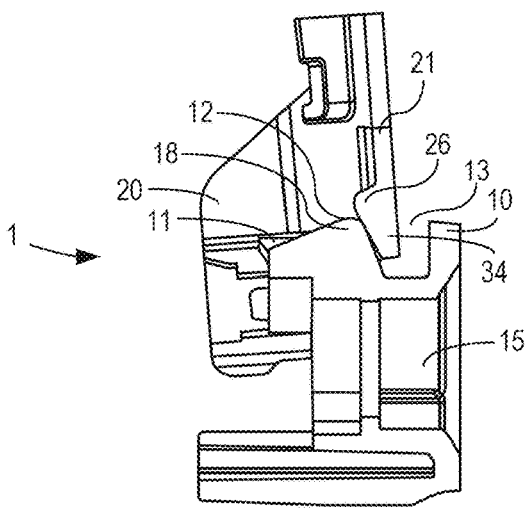
FIG. 11C illustrates the frictional engagement of the flexible tab of the protective shield with the cam member of the ring, when the protective shield is in the retracted position.

In reference to FIGS. 11A and 11B, further rotation of the protective shield 20 may cause the rib 26 of the flexible tab 21 to slide onto the lug 11 of the ring 10, and get to the other side of the lug 11, called proximal side 19*b*, located distally relative to the proximal side 19*b*. At the end of the rotating movement, the protective shield 20 is in the retracted position, thereby uncovering the needle tip 104. This situation is illustrated in FIG. 11C. A proximal portion of the protective shield 20 may be accommodated in the groove 13. The longitudinal axis of the protective shield 20 may be oblique or substantially perpendicular to the axis of the ring 10. The flexible tab 21 may be oblique or perpendicular to the axis of the ring 10. The flexible tab 21 may remain located radially outwardly relative to the lug 11, with regard to the axis of the ring 10, and the proximal end 34 of the flexible tab 21 may face the groove 13 of the ring 10.

The protective shield 20 may be prevented from moving from the retracted position, in particular from moving back to the storage position or from moving to the safety position, by frictional engagement of the rib 26 with the cam member 12. In more details, the flexibility of the flexible tab 21 urges the flexible tab 21 towards the cam member 12, which may improve the frictional engagement between them. The protective shield 20 may be secured to the retracted position, unless a determined effort is applied by the user onto the protective shield 20. Hence, the user has to push the protective shield 20 with a certain effort to overcome the blocking resulting from the frictional engagement to move the protective shield 20 away from the retracted position, in particular to the safety position. The subsequent injection step thus may be made without the need for the user to handle the protective shield 20 for preventing unexpected tilt of the protective shield 20 during the injection, thereby making the injection safer.

The rib 26 and the cam member 12 may be configured to maintain the protective shield 20 at an angle superior or equal to 80°, preferably to 90°, relative to the axis of the ring 10 when the protective shield 20 is in the retracted position. Possible adjustments may include, for example, the dimensions of the rib 26 and the cam member 12, and the inclination of the rib 26 and the cam member 12 relative to each other. Maintaining the protective shield 20 at an angle superior or equal to 90° may allow for completely uncovering the needle 101, thereby making the needle 101 visible for the user and facilitating the injection.

The rib 26 and the cam member 12 are configured so that, when the protective shield 20 is in the retracted position, the distal end of the protective shield 20 does not protrude from the needle tip 104. In that way, the injection is not disrupted by contact of the protective shield 20 with the skin of the patient. After the injection, the user may rotate the protective shield 20 around the pivot axis of the hinge, towards the needle 101, into the safety position, as illustrated in FIGS. 11A, 11B, and 11C. The needle tip 104 is thereby covered by the protective shield 20, and any pricking of the user or any person around by the needle tip is thus prevented.

Rotation of the protective shield 20 around the pivot axis causes the proximal end 34 of the flexible tab 21 to engage the lug 11 of the ring 10. The flexible tab 21 is located radially outwardly from the lug 11, relative to the axis of the ring 10, and may abut the radially outward side of the lug 11. The flexible tab 21 may be subjected to flexural deformation by deflecting radially outwardly from the body 22 of the protective shield 20. Further rotation of the protective shield 20 may cause the flexible tab 21 to slide on the lug 11 of the ring 10, until the flexible tab 21 passes the lug 11 and gets to the radially inward side of the lug 11. At the end of the rotating movement, the protective shield 20 is in the safety position, and covers at least the needle tip 104.

Figure 12A:
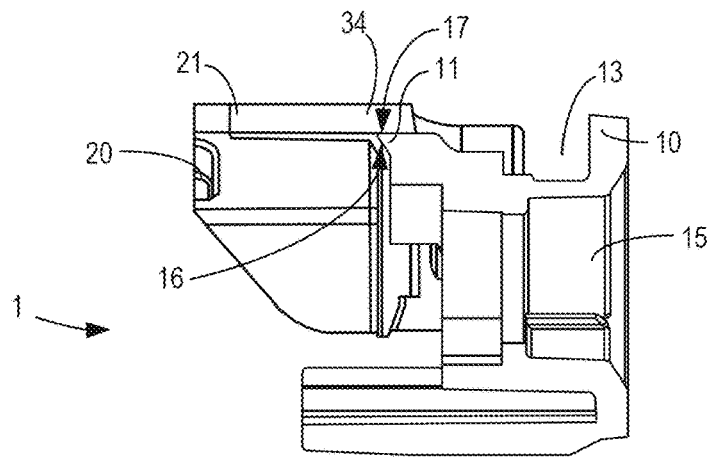
FIG. 12A is a side sectional view of the safety device, wherein the protective shield is in the storage position.
Figure 12B:
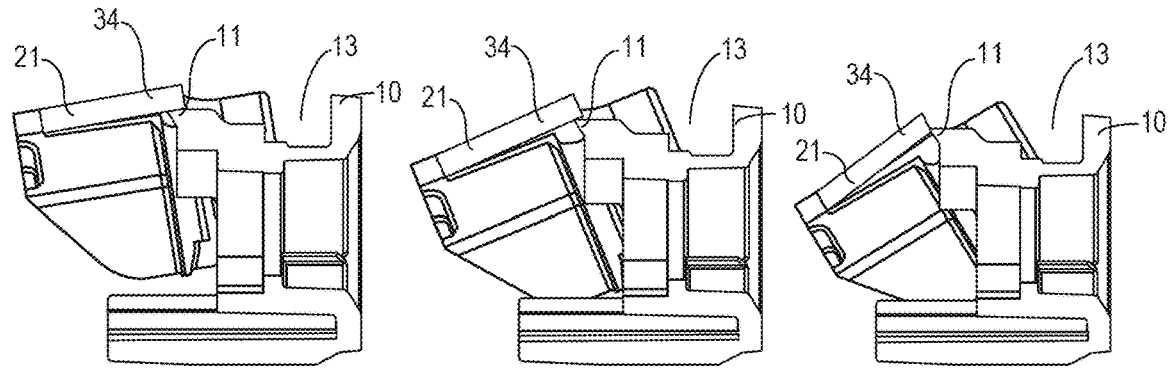
FIG. 12B illustrates the transition of the protective shield from the storage position to the safety position.
Figure 12C:
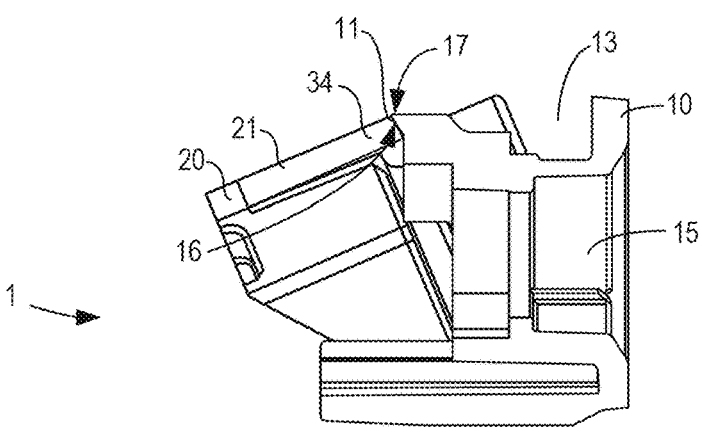
FIG. 12C illustrates the buckling deformation of the flexible tab of the protective shield when the protective shield is in the safety position.
Figure 13:
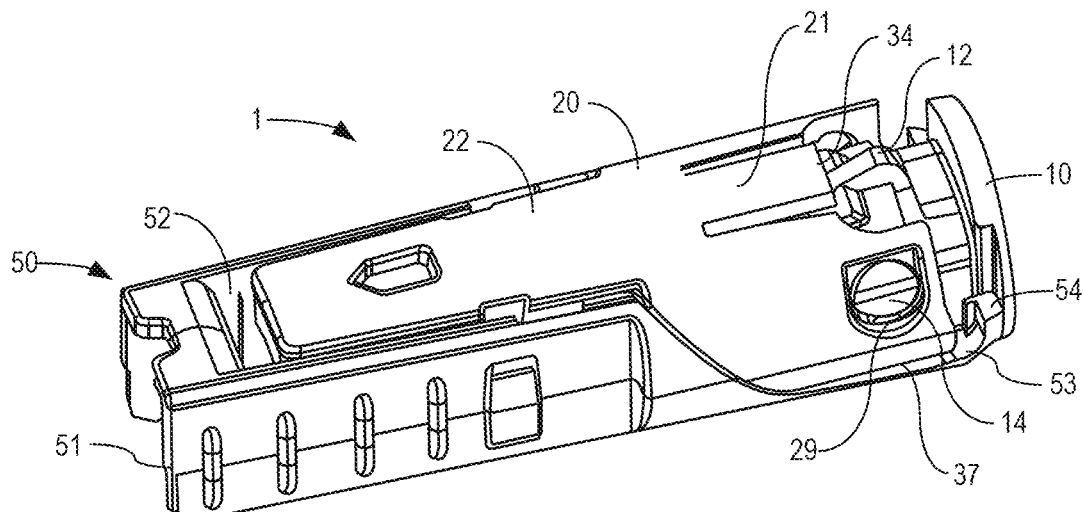
FIG. 13 is a general perspective view of the safety device of a non-limiting embodiment, provided with a protective cap.

As illustrated in FIG. 12C, the longitudinal axis of the protective shield 20 may be oblique relative to the axis of the ring 10. The flexible tab 21 may be oblique relative to the axis of the ring 10.

The flexible tab 21 may be located radially inwardly relative to the lug 11, with regard to the axis of the ring 10, and the proximal end 34 of the flexible tab 21 faces the lug 11. The needle 101 may be locked into the protective shield 20 by the hook, and the needle tip 104 may be accommodated inside the notch. Therefore, the needle tip 104 is covered and any pricking of a person by the needle may be prevented. The protective shield 20 may be prevented from moving from the safety position, in particular from moving back to the storage position or the retracted position, by abutment of the proximal end 34 of the flexible tab 21 against the lug 11 which may cause the flexible tab 21 to undergo buckling deformation. This buckling deformation impedes disengagement of the flexible tab 21 from the lug 11. As a consequence, the protective shield 20 is secured to the safety position, and the safety device 1 can no longer be used for another injection. When abutting the needle 101, the protective shield 20 may be further pushed by the user to continue the rotating movement, so that at least the needle tip 104 deforms under the pressure exerted by the user. This position also corresponds to the safety position. As a consequence, the deformed needle tip 104 may lie against the protective shield 20, parallel to and in contact with the inner surface 30 of the protective shield 20, which may further improve the safety by totally covering the needle tip. In some non-limiting embodiments or aspects, the flexible tab 21 may lock the protective shield 20 in the safety position, and may also maintain the protective shield 20 in the retracted position before the injection.

Figure 14:
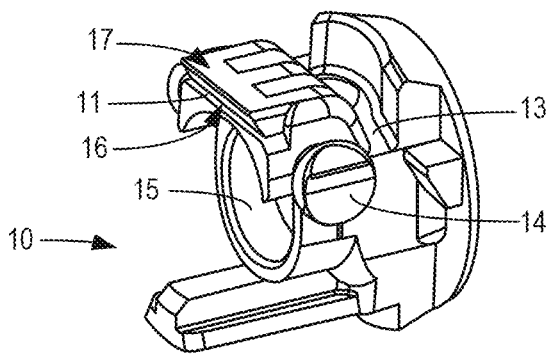
FIG. 14 is a general perspective view of the ring according to a non-limiting embodiment of the safety device.
Figure 15:
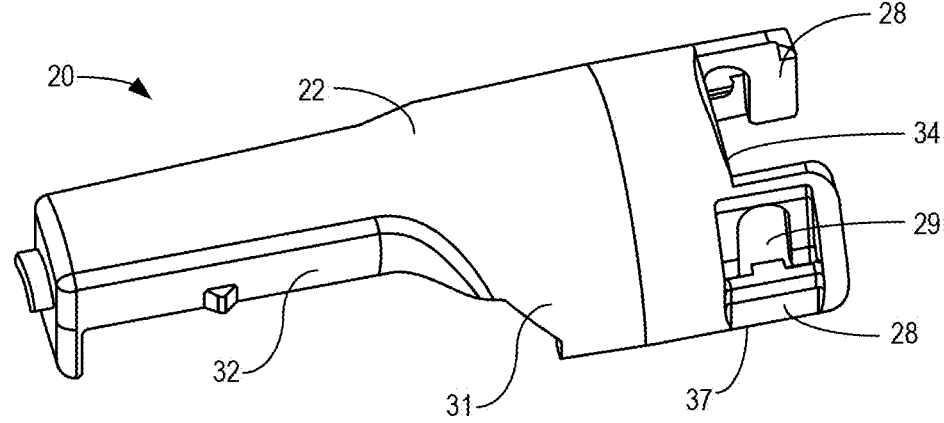
FIG. 15 is a general perspective view of the protective shield according to a non-limiting embodiment.
Figure 16:
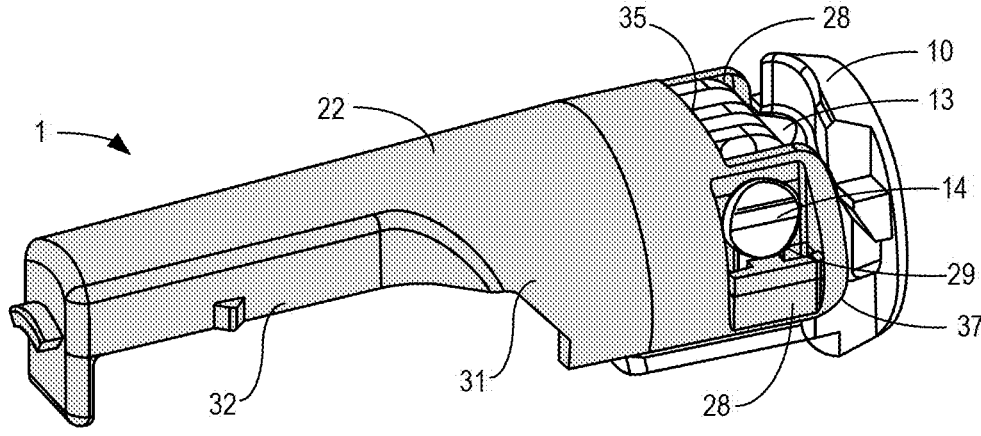
FIG. 16 is a general view of the safety device comprising the protective shield of FIG. 15 pivotably mounted onto the ring of FIG. 14.

According to non-limiting embodiments or aspects, the safety device 1 is illustrated in FIGS. 16, 17A-C, and 18, wherein the safety device 1 may include the ring 10 illustrated in FIG. 14 and the protective shield 20 illustrated in FIG. 15. The general structures of the ring 10 and protective shield 20 of some non-limiting embodiments may be the same as or similar to that of non-limiting embodiments described before, and will not be further described. The common features between non-limiting embodiments represented in FIGS. 8-10, 11A-C, 12A-C, and 14-16, 17A-C and 18, are given the same references.

In some non-limiting embodiments or aspects, the first hinge portion of the ring 10 may include two colinear pins 14 that define a pivot axis of the protective shield 20. The ring 10 may include a lug 11 which protrudes from the outer surface of the ring 10, and a groove 13. Each pin 14 of the ring 10 is configured to engage a respective opening 29 of the protective shield 20, thereby forming a hinge wherein the protective shield 20 is pivotably movable relative to the ring 10 around a pivot axis joining the center of the pins 14. The locking member of the protective shield 20 does not comprise any flexible tab. The engagement of the protective shield 20 with the lug 11 of the ring 10 is achieved via a proximal contacting end 35 of the protective shield 20 from which the proximal legs extends, the proximal contacting end 35 being the locking member.

In some non-limiting embodiments or aspects, the user may have a clearer feeling of the locking of the protective shield 20 in the safety position, since the engagement of the locking member with the lug 11 is less smooth than with a flexible leg. The functioning of the safety device 1 according to non-limiting embodiments will now be described, in reference to FIGS. 17A, 17B, and 17C.

Figure 17A:
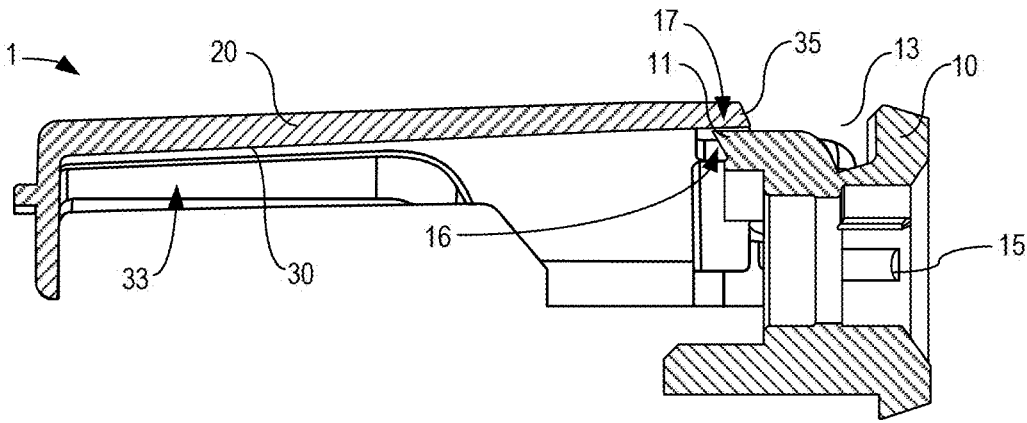
FIG. 17A is a side sectional view of the safety device, wherein the protective shield is in the storage position.
Figure 17B:
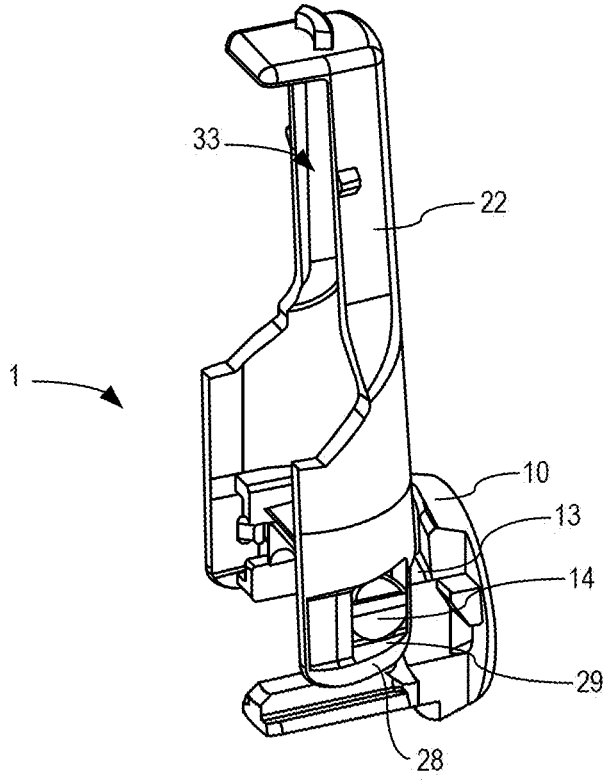
FIG. 17B is a perspective view of the safety device, wherein the protective shield is in the retracted position.

FIG. 17A corresponds to the configuration of the safety device 1 before its use. In this configuration, the protective shield 20 is in the storage position wherein it covers the needle tip 104. The longitudinal axis of the protective shield 20 may be parallel to the axis of the ring 10. The proximal contacting end 35 may extend parallel to the axis of the ring 10. The proximal contacting end 35 may be located radially outwardly from the lug 11, relative to the axis of the ring 10, and may cover the radially outward side 17 of the lug 11.

Figure 17C:
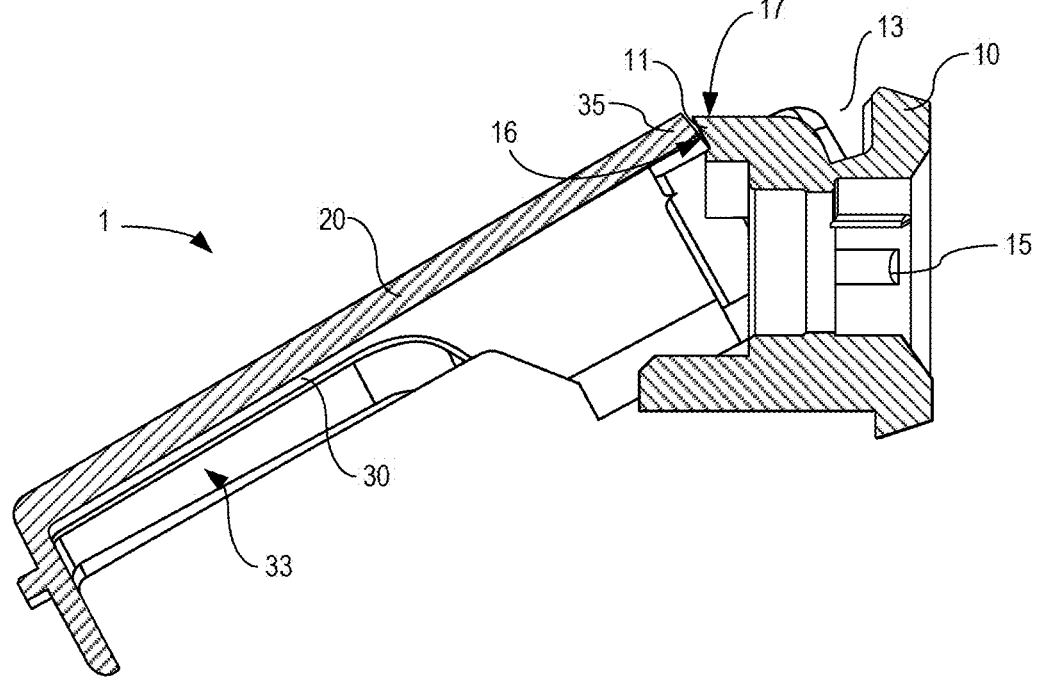
FIG. 17C is a side sectional view of the safety device, wherein the protective shield is in the safety position.
Figure 18:
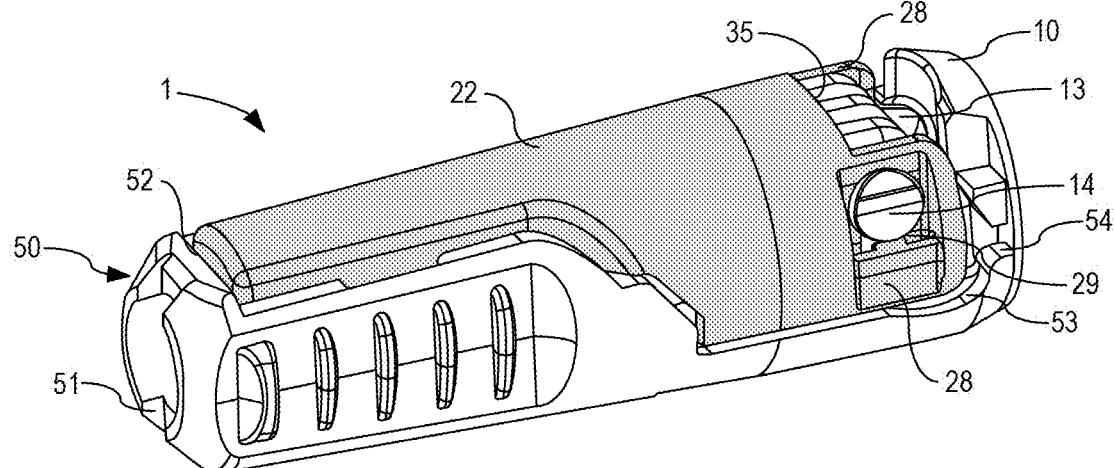
FIG. 18 is a general view of the safety device of a non-limiting embodiment, provided with a protective cap.

In order to use the safety assembly 200, the user draws the protective cap 50 in the distal direction. The removal of the protective cap 50 triggers the rotation of the protective shield 20 around the pivot axis of the hinge, relative to the pins 14 of the ring 10, away from the storage position. The protective shield 20 may further rotate up to the retracted position illustrated in FIG. 17B. The safety device 1 is configured so that removal of the protective cap 50 may cause the protective shield 20 to pivot about the hinge up to its retracted position. The proximal contacting end 35 may be accommodated in the groove 13. In the retracted position, the needle tip 104 may be uncovered and physically accessible, and the safety assembly 200 is ready for the injection of the composition contained in the medical injection device 100. The longitudinal axis of the protective shield 20 may be oblique or substantially perpendicular to the axis of the ring 10. The proximal contacting end 35 may remain located radially outwardly relative to the lug 11, with regard to the axis of the ring 10, and may face the groove 13 of the ring 10. After the injection, the user drives the protective shield 20 around the pivot axis of the hinge, towards the needle 101, into the safety position, as illustrated in FIG. 17C. The needle tip 104 may be covered by the protective shield 20, and any pricking of the user or any person around by the needle tip 104 is thus prevented.

Rotation of the protective shield 20 around the pivot axis may cause the proximal contacting end 35 of the protective shield 20 to engage the lug 11 of the ring 10. The proximal contacting end 35 may be located radially outwardly from the lug 11, relative to the axis of the ring 10, and may abut the radially outward side 17 of the lug 11. The first and second hinge portions may be subjected to flexural deformation which allows the rotation of the protective shield 20. Further rotation of the protective shield 20 may cause the proximal contacting end 35 to slide on the lug 11 of the ring 10 until the proximal contacting end 35 passes the lug 11 and gets to the radially inward side 16 of the lug 11. At the end of the rotating movement, the protective shield 20 is in the safety position, and covers at least the needle tip 104.

As illustrated in FIG. 17C, the longitudinal axis of the protective shield 20 is oblique relative to the axis of the ring 10. The proximal contacting end 35 is oblique relative to the axis of the ring 10. The proximal contacting end 35 may be located radially inwardly relative to the lug 11, with regard to the axis of the ring 10, and the proximal contacting end 35 may face the lug 11. The needle 101 may be locked into the protective shield 20 by the hook, and the needle tip 104 may be accommodated inside the notch 33.

The protective shield 20 may be further locked on the needle 101 by the hook, and the needle tip 104 may be accommodated inside the notch 33. Therefore, the needle tip 104 may be covered and any pricking of a person by the needle is prevented. The protective shield 20 may be prevented from moving from the safety position, in particular from moving back to the storage position or the retracted position, by abutment of the proximal contacting end 35 against the lug 11 which may cause the first and second hinge portions to undergo buckling deformation. This buckling deformation may impede disengagement of the proximal contacting end 35 from the lug 11. As a consequence, the protective shield may be secured to the safety position, and the safety device can no longer be used for another injection. When abutting the needle 101, the protective shield 20 may be further pushed by the user to continue the rotating movement, so that at least the needle tip 104 deforms under the pressure exerted by the user. This position also corresponds to the safety position. As a consequence, the deformed needle tip 104 may lie against the protective shield 20, parallel to and in contact with the inner surface 30 of the protective shield 20, which may further improve the safety by totally covering the needle tip.

In some non-limiting embodiments or aspects, the locking of the protective shield 20 by the locking member 12 or proximal contacting end 35 may take place in the alignment of the locking member 12. Therefore, the radial size of the safety assembly does not increase, which does not limit its packaging, for example in nests. It should be noted that the non-limiting embodiments described above are not limited to a specific design of the hinge. Moreover, non-limiting embodiments of the first hinge portion may be associated with non-limiting embodiments of the second hinge portion, as long as their structure is compatible and the safety device works and achieves the locking of the protective shield 20 in the safety position as described previously. For example, the protective shield 20 of non-limiting embodiments, provided with the proximal contacting end 35 (with no flexible tab) may be combined with the axle 27 and groove 13 of other non-limiting embodiments.

The invention claimed is:

1. A safety device for a medical injection device, comprising:

a ring configured to be attached to a distal tip of a medical injection device and comprising a first hinge portion; and a protective shield comprising a second hinge portion pivotally coupled to the first hinge portion, the protective shield configured to adopt successively a storage position in which the protective shield covers the needle tip, a retracted position in which the protective shield uncovers the needle tip, and a safety position in which the protective shield covers the needle tip;

wherein:

the ring comprises a lug, the lug extending distally and comprising an internal side and an external side opposite to the internal side, wherein the internal side is closer to a center point of the ring than the external side;

the protective shield comprises at least one proximal locking member;

in the safety position, the protective shield is locked on the ring by engagement of the locking member with the lug;

the locking member is a flexible tab, wherein the flexible tab extends primarily axially and proximally directly from the body of the protective shield, wherein an axial direction is defined as a longitudinal axis of the protective shield; and the locking member is configured to:

engage the lug when the protective shield transitions from the retracted position to the safety position, so that the locking member abuts against the external side of the lug and deflects radially outwardly, relative to the axis of the ring wherein the axis of the ring extends through the center point of the ring in a manner that is perpendicular to a radius of the ring, from a body of the protective shield when the protective shield passes from the external side of the lug to the internal side of the lug, and remain engaged with the internal side of the lug for maintaining the protective shield in the safety position.

2. The safety device according to claim 1, wherein the locking member comprises a single flexible tab.

3. The safety device according to claim 2, wherein:

the flexible tab comprises an inner surface provided with a rib, and the ring comprises a protrusion provided with a cam member, the protrusion extending radially from the ring and comprising a distal side and a proximal side located proximally relative to the distal side, the flexible tab is configured to deform in flexion by engagement of the rib with the cam member when the protective shield transitions from the storage position to the retracted position, so that the rib passes from the distal side of the lug to the proximal side of the lug, and the rib is configured to remain engaged with the cam member for maintaining the protective shield in the retracted position.

4. The safety device according to claim 3, wherein the rib and the cam member are configured to maintain the protective shield at an angle equal to or greater than 80° relative to an axis of the ring when the protective shield is in the retracted position.

5. The safety device according to claim 1, wherein the locking member comprises two flexible tabs separated by a slot.

6. The safety device according to claim 5, wherein each flexible tab comprises a free end separated from the body of the protective shield by a respective groove opposite the slot.

7. The safety device according to claim 1, wherein the flexible tab protrudes proximally from the lug when the protective shield is in the storage position and/or in the safety position.

8. The safety device according to claim 1, wherein the flexible tab extends toward the second hinge portion.

9. The safety device according to claim 1, wherein: the first hinge portion comprises a groove defining a pivot axis of the protective shield, and the protective shield comprises an axle clipped into the groove.

10. The safety device according to claim 1, wherein: the first hinge portion comprises two colinear pins defining a pivot axis of the protective shield, and the protective shield comprises two proximal legs provided with an opening, each colinear pin engaging a respective opening of the two proximal legs.

11. The safety device according to claim 1, further comprising a protective cap configured to be mounted onto a distal tip of a medical injection device to cover a needle tip thereof, wherein the protective shield is interlocked with the protective cap when the protective shield is in the storage position.

12. The safety device according to claim 1, further comprising:

a medical injection device comprising a barrel, a distal tip extending distally from the barrel, and a needle mounted onto the distal tip, wherein the ring is around the distal tip of the medical injection device.

13. The safety device according to claim 1, wherein:

the flexible tab comprises an inner surface provided with a rib, and the ring comprises a protrusion provided with a cam member, the protrusion extending radially from the ring and comprising a distal side and a proximal side located proximally relative to the distal side, the flexible tab is configured to deform in flexion by engagement of the rib with the cam member when the protective shield transitions from the storage position to the retracted position, so that the rib passes from the distal side of the lug to the proximal side of the lug, and the rib is configured to remain engaged with the cam member for maintaining the protective shield in the retracted position.

14. The safety device according to claim 13, wherein the rib and the cam member are configured so that, when the protective shield is in the retracted position, the distal end of the protective shield does not protrude from the needle tip.

15. A safety device for a medical injection device, comprising:

a ring configured to be attached to a distal tip of a medical injection device and comprising a first hinge portion; and a protective shield comprising a second hinge portion pivotally coupled to the first hinge portion, the protective shield configured to adopt successively a storage position in which the protective shield covers the needle tip, a retracted position in which the protective shield uncovers the needle tip, and a safety position in which the protective shield covers the needle tip;

wherein:

the ring comprises a lug, the lug extending distally and comprising an internal side and an external side opposite to the internal side, wherein the internal side is closer to a center point of the ring than the external side;

the protective shield comprises at least one proximal locking member;

in the safety position, the protective shield is locked on the ring by engagement of the locking member with the lug;

the locking member is a flexible tab, wherein the flexible tab extends primarily axially and proximally directly from the body of the protective shield, wherein an axial direction is defined as a longitudinal axis of the protective shield; and the locking member is configured to:

engage the lug when the protective shield transitions from the retracted position to the safety position, so that the locking member abuts against the external side of the lug and deflects radially outwardly, relative to the axis of the ring wherein the axis of the ring extends through the center point of the ring in a manner that is perpendicular to a radius of the ring, from a body of the protective shield when the protective shield passes from the external side of the lug to the internal side of the lug, and remain engaged with the internal side of the lug for maintaining the protective shield in the safety position by abutment of the flexible tab against the internal side of the lug such that the locking member undergoes buckling deformation.

16. The safety device according to claim 15, further comprising a protective cap configured to be mounted onto a distal tip of a medical injection device to cover a needle tip thereof, wherein in the storage position:

the protective shield is interlocked with the protective cap, and the needle tip is embedded in the protective cap, the protective cap is configured to engage with both the protective shield and the needle tip to maintain the storage position, such that removal of the protective cap in a distal direction causes the protective shield to transition into the retracted position.

\* \* \* \* \*